(12) United States Patent
Yang et al.

(10) Patent No.: US 9,116,034 B2
(45) Date of Patent: Aug. 25, 2015

(54) WIRELESS MEASUREMENT DEVICE USING SURFACE ACOUSTIC WAVE (SAW)-BASED MICRO SENSOR AND METHOD OF USING THE SAW-BASED MICRO SENSOR

(75) Inventors: Sang Sik Yang, Seoul (KR); Ik Mo Park, Gyeonggi-do (KR); Young kil Kim, Seoul (KR); Kee Keun Lee, Gyeonggi-do (KR); Ick Jin Kwon, Gyeonggi-do (KR); Hae Kwan Oh, Gyeonggi-do (KR)

(73) Assignee: AJOU UNIVERSITY INDUSTRY COOPERATION FOUNDATION, Gyeonggi-Do (KR)

( * ) Notice: Subject to any disclaimer, the term of this patent is extended or adjusted under 35 U.S.C. 154(b) by 294 days.

(21) Appl. No.: 13/824,005

(22) PCT Filed: Sep. 14, 2011

(86) PCT No.: PCT/KR2011/006775
§ 371 (c)(1),
(2), (4) Date: Mar. 15, 2013

(87) PCT Pub. No.: WO2012/036460
PCT Pub. Date: Mar. 22, 2012

(65) Prior Publication Data
US 2013/0174662 A1 Jul. 11, 2013

(30) Foreign Application Priority Data
Sep. 17, 2010 (KR) .......................... 10-2010-0092034

(51) Int. Cl.
*G01N 29/00* (2006.01)
*G01H 17/00* (2006.01)
(Continued)

(52) U.S. Cl.
CPC ............... *G01H 17/00* (2013.01); *G01D 21/00* (2013.01); *G01L 1/165* (2013.01); *G01L 9/0025* (2013.01);
(Continued)

(58) Field of Classification Search
CPC ............ G01N 29/022; G01N 29/2462; G01N 29/2481; G01N 29/036; G01N 29/4481; G01N 29/2468
USPC ..................................... 73/649, 579, 580, 602
See application file for complete search history.

(56) References Cited

U.S. PATENT DOCUMENTS 4,535,632 A * 8/1985 Sinha et al. ..................... 73/703
6,848,295 B2 * 2/2005 Auner et al. .................. 73/24.06
(Continued)

FOREIGN PATENT DOCUMENTS

| JP | 2004-320319 | 11/2004 |
| JP | 2005-121498 | 5/2005 |

(Continued)

OTHER PUBLICATIONS

International Search Report (ISR) in PCT/KR2011/006775, dated Mar. 26, 2012, with English Translation.

*Primary Examiner* — Helen Kwok
(74) *Attorney, Agent, or Firm* — Harness, Dickey & Pierce, P.L.C.

(57) ABSTRACT

A wireless measurement device includes a sound acoustic wave (SAW)-based micro sensor converting a wirelessly received pulse signal into an SAW and generating a plurality of pulse signals by reflecting the SAW, and wirelessly transmitting the plurality of pulse signals to measure a variance of an environmental element; and a reader generating and wirelessly transmitting a pulse signal to the SAW-based micro sensor to measure variances in environmental elements.

6 Claims, 2 Drawing Sheets

(51) Int. Cl.
*G01N 29/02* (2006.01)
*G01N 29/24* (2006.01)
*G06K 19/067* (2006.01)
*G06K 19/07* (2006.01)
*G01D 21/00* (2006.01)
*G01L 9/00* (2006.01)
*G01L 1/16* (2006.01)

(52) U.S. Cl.
CPC .......... *G01N 29/022* (2013.01); *G01N 29/2481* (2013.01); *G06K 19/0675* (2013.01); *G06K 19/0717* (2013.01); *G01N 2291/0256* (2013.01); *G01N 2291/0423* (2013.01)

(56) References Cited

U.S. PATENT DOCUMENTS

| | | | |
|---|---|---|---|
| 7,017,404 B1* | 3/2006 | Kain | 73/146.5 |
| 7,040,139 B2* | 5/2006 | Sunshine | 73/23.2 |
| 7,096,736 B2* | 8/2006 | Pfeifer et al. | 73/715 |
| 7,146,861 B1* | 12/2006 | Cook et al. | 73/718 |
| 7,151,437 B2 | 12/2006 | Fukuda | |
| 7,253,725 B2* | 8/2007 | Breed et al. | 340/447 |
| 8,960,004 B2* | 2/2015 | Zaghloul et al. | 73/579 |
| 2003/0005759 A1* | 1/2003 | Breed et al. | 73/146 |
| 2006/0032290 A1* | 2/2006 | Liu | 73/29.02 |
| 2006/0075820 A1* | 4/2006 | Cobianu et al. | 73/703 |
| 2006/0230833 A1* | 10/2006 | Liu et al. | 73/649 |
| 2006/0230834 A1* | 10/2006 | Liu et al. | 73/649 |
| 2006/0243064 A1* | 11/2006 | Liu et al. | 73/861.25 |
| 2006/0283247 A1* | 12/2006 | Liu et al. | 73/514.01 |
| 2006/0283252 A1* | 12/2006 | Liu et al. | 73/649 |
| 2007/0039371 A1* | 2/2007 | Omata et al. | 73/9 |
| 2007/0107519 A1* | 5/2007 | Liu et al. | 73/649 |
| 2008/0127729 A1* | 6/2008 | Edmonson et al. | 73/599 |
| 2009/0193897 A1* | 8/2009 | Serban et al. | 73/584 |

FOREIGN PATENT DOCUMENTS

| | | |
|---|---|---|
| JP | 2008-204234 | 9/2008 |
| KR | 10-2007-0096217 | 10/2007 |

* cited by examiner

WIRELESS MEASUREMENT DEVICE USING SURFACE ACOUSTIC WAVE (SAW)-BASED MICRO SENSOR AND METHOD OF USING THE SAW-BASED MICRO SENSOR

CROSS-REFERENCE TO RELATED APPLICATIONS

This application is a national phase application of PCT Application No. PCT/KR2011/006775, filed on Sep. 14, 2011, which claims the benefit and priority to Korean Patent Application No. 10-2010-0092034, filed Sep. 17, 2010. The entire disclosures of the applications identified in this paragraph are incorporated herein by references.

TECHNICAL FIELD

The present invention relates to a wireless measurement device using a surface acoustic wave (SAW)-based micro sensor and a method of using the SAW-based micro sensor, and more particularly, to technology of measuring variances in environmental elements such as a temperature, gases, and pressure by using a SAW-based micro sensor.

BACKGROUND

Recently, surface acoustic wave (SAW)-based micro sensors are generally used for tire-pressure monitoring systems, temperature sensors, biosensors, and environmental gas sensors. SAW-based micro sensors have more merits than semiconductor-based micro sensors.

First, since an SAW is generated on a surface of a micro sensor by using radio frequency (RF) energy wirelessly supplied from the outside and variances in a time, a phase, and an amplitude of the SAW reflected by a reflector and returns, a battery is not necessary.

Second, since it is not necessary to equip a semiconductor integrated circuit (IC) chip, it is possible to maintain stable properties for a long time in a rough and poor environment such as a high temperature, humidity, and impacts. Third, long distance wireless communication is possible with RF energy supplied from the outside. Fourth, in a quickly rotating and moving range such as in a tire of a vehicle, it is possible to sense factors in real time.

A measurement of variances in environmental elements by using SAW-based micro sensors may be divided into two ways. One is a method of measuring a variance of a resonance frequency of an SAW-based micro sensor caused by an environmental element, and another is a method of measuring a variance of a reflection peak reflected by an SAW-based micro sensor and returning.

Among them, since the method of measuring the variance of the resonance frequency of the SAW-based micro sensor needs an inter-digital transducer (IDT), there is a limitation in wireless measurements. Accordingly, the method of measuring the variance of the reflection peak reflected and returning is appropriate for wireless measurements. Such variances of reflection peaks may be measured by using network analyzers. However, since network analyzers are expensive and have large sizes, there is a limitation in being actually applied to industrial fields. Accordingly, it is necessary to provide small sized cheap wireless measurement devices.

Such small sized cheap wireless measurement devices employ a method of measuring variances of environmental elements by measuring time delays of SAWs returning from SAW-based micro sensors. However, to measure very short time delays, that is, to measure minute variances in environmental elements, in other words, to have high resolution, small sized cheap wireless measurement devices are equipped with expensive elements capable of generating clocks of several GHz-frequency. Due to this, prices of wireless measurement devices using time delays are increased.

DISCLOSURE OF THE INVENTION

Technical Problem

An aspect of the present invention provides a wireless measurement device capable of measuring minute variances in environmental elements by using a surface acoustic wave (SAW)-based micro sensor with no expensive element for generating clocks of a frequency of several GHz and a method of using the SAW-based micro sensor.

Technical Solution

According to an aspect of the present invention, a wireless measurement device includes a sound acoustic wave (SAW)-based micro sensor converting a wirelessly received pulse signal into an SAW and generating a plurality of pulse signals by reflecting the SAW, and wirelessly transmitting the plurality of pulse signals to measure a variance of an environmental element and a reader generating and wirelessly transmitting a pulse signal to the SAW-based micro sensor to measure variances in environmental elements, whenever an interval between the plurality of pulse signals received by reflecting the transmitted pulse signal by the SAW micro sensor is corresponding to a determined interval between pulse signals of an environmental element, the reader generating and wirelessly transmitting a pulse signal to the SAW-based micro sensor and measuring a variance in the environmental element by counting times of pulse signals generated for a certain amount of time.

The SAW-based micro sensor may include an antenna wirelessly transmitting and receiving a pulse signal, an inter-digital transducer (IDT) generating an SAW by applying the pulse signal received at the antenna to a plurality of metallic electrodes formed parallel to one another and converting a plurality of SAWs reflected by the reflector part into a plurality of pulse signals, and wirelessly outputs the plurality of pulse signals via the antenna, and the reflector part including a plurality of reflectors and reflecting the SAW generated by the IDT.

The IDT may have a single phase unidirectional transducer configuration.

The reader may include an environmental element variance measurement part generating and transmitting a pulse signal for measuring a variance of an environmental element to the SAW-based micro sensor via an radio frequency (RF) part, whenever an interval between the plurality of pulse signals received by reflecting the transmitted pulse signal by the SAW micro sensor is corresponding to a determined interval between pulse signals of an environmental element, the environmental element variance measurement part generating and wirelessly transmitting a pulse signal to the SAW-based micro sensor via the RF part and measuring a variance in the environmental element by counting times of pulse signals generated for a certain amount of time and the RF part wirelessly transmitting the pulse signal generated by the environmental element variance measurement part to the SAW-based micro sensor and transmitting the plurality of pulse signals wirelessly received from the SAW-based micro sensor to the environmental element variance measurement part.

The RF part may include an antenna wirelessly transmitting and receiving a pulse signal, a transmitter modulating the pulse signal generated by the environmental element variance measurement part and transmitting the modulated signal to the SAW-based micro sensor via the antenna, and a receiver modulating the plurality of pulse signals reflected by the SAW-based micro sensor and received via the antenna ANT and transmitting the modulated signals to the environmental element variance measurement part.

According to another aspect of the present invention, a method of wirelessly measuring by using an SAW-based micro sensor includes generating a pulse signal and wirelessly transmitting the pulse signal to the SAW-based micro sensor, performed by a reader, to measure a variance of an environmental element, converting the wirelessly received pulse signal into an SAW, and to measure the variance of the environmental element, generating a plurality of pulse signals by reflecting the SAW, and wirelessly transmitting the plurality of pulse signals, performed by an SAW-based micro sensor, and generating and wirelessly transmitting a pulse signal to the SAW-based micro sensor and measuring the variance of the environmental element by counting times of pulse signals generated for a certain amount of time whenever an interval between the plurality of pulse signals received by reflecting the transmitted pulse signal by the SAW micro sensor is corresponding to a determined interval between pulse signals of the environmental element, performed by the reader.

Advantageous Effects

In a wireless measurement device using a sound acoustic wave (SAW)-based micro sensor and a method of using the SAW-based micro sensor according to an embodiment of the present invention, whenever an interval between the plurality of pulse signals received by reflecting the transmitted pulse signal by the SAW micro sensor is corresponding to a determined interval between pulse signals of an environmental element, a pulse signal is generated and wirelessly transmitted to the SAW-based micro sensor and a variance in the environmental element is measured by counting times of pulse signals generated for a certain amount of time, a minute variance in an environmental element may be measured by using the SAW-based micro sensor capable of being easily portable with no expensive elements generating clocks of a frequency of several GHz.

MODE FOR CARRYING OUT THE INVENTION

Hereinafter, exemplary embodiments of the present invention will now be described in detail with reference to the attached drawings. In describing the embodiments of the present invention, a detailed description of related well-known functions or configurations will be omitted when the description is considered as making the subject matter of the present invention unclear. Also, terms that will be described below are defined considering functions in the embodiments, which may vary with purposes of user and operators or customs. Therefore, the definition thereof will be done based on the contents of the entire present specification.

Figure 1:
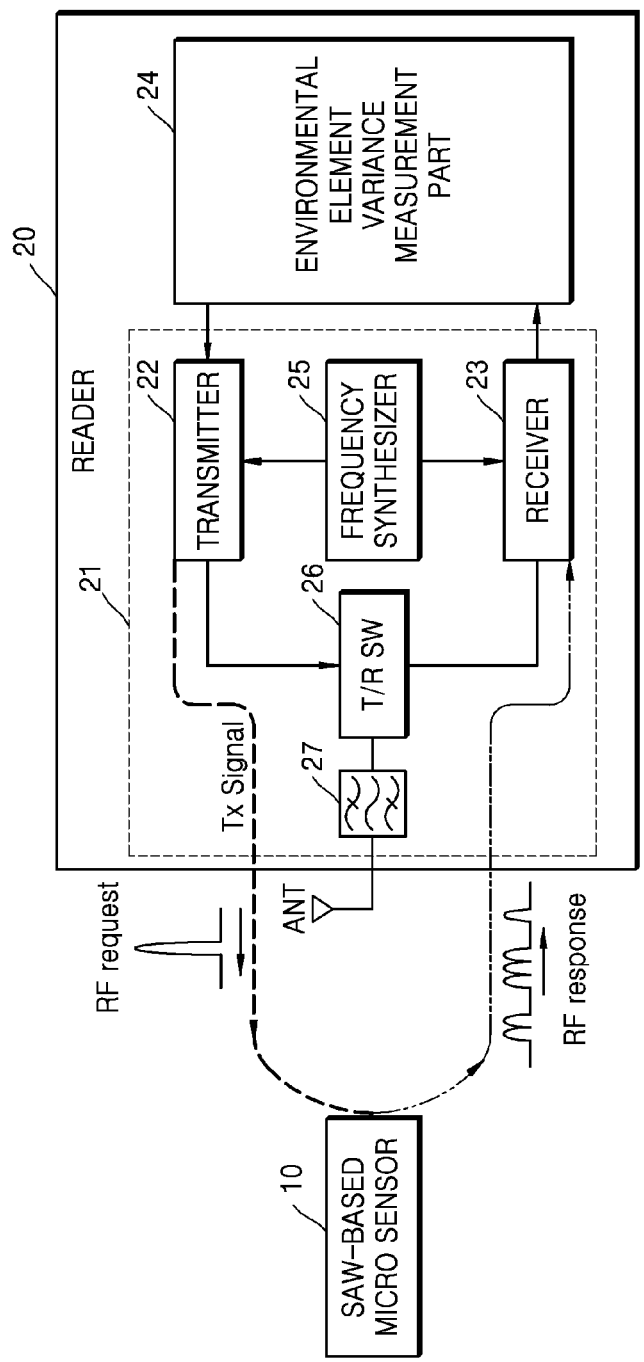
FIG. 1 is a configuration view illustrating a wireless measurement device using a surface acoustic wave (SAW)-based micro sensor according to an embodiment of the present invention.

FIG. 1 is a configuration view illustrating a wireless measurement device using a surface acoustic wave (SAW)-based micro sensor 10 according to an embodiment of the present invention.

As shown in the drawing, the wireless measurement device may include the SAW-based micro sensor 10 and a portable reader 20.

The SAW-based micro sensor 10 converts a pulse signal wirelessly received into an SAW, reflects the SAW to measure variances in environmental elements, and generates and wirelessly transmits a plurality of pulse signals. In this case, the environmental elements may be pressure, a temperature, humidity, etc.

The SAW-based micro sensor 10 includes a substrate (not shown), an antenna (not shown), an inter-digital transducer (IDT), and a reflector part (not shown) including a plurality of reflectors to measure the variances in the environmental elements. The substrate may be formed of a material having piezoelectricity. As an example of the material, LiNbO3, LiTaO3, quartz, etc may be used. Particularly, the substrate may be 41o YX LiNbO3 piezoelectric substrate having high SAW propagation velocity and a great electrochemical coupling element. The high SAW speed allows patterning of a device while being manufactured to be easy. Also, the great electrochemical coupling element allows high reflectivity from the reflectors and a low insertion loss.

The antenna wirelessly transmits and receives a pulse signal. The antenna may transmit and receive the pulse signal via a communication in a frequency band with an intermediate frequency of 2.4 GHz.

The IDT generates an SAW by applying the pulse signal received at the antenna to a plurality of metallic electrodes formed parallel to one another and converts a plurality of SAWs reflected by the reflector part into a plurality of pulse signals, and wirelessly outputs the plurality of pulse signals via the antenna. The SAW reflected by the reflector part as described above are a plurality thereof because the SAW is reflected by the plurality of reflectors included in the reflector part, respectively. Since the IDT has a single phase unidirectional transducer configuration in such a way that the SAW is not propagated with the IDT centered but is propagated in one direction, thereby minimizing energy of the applied pulse signal.

The reflector part includes the plurality of reflectors and reflects the SAW generated by the IDT.

The reader 20 generates and wirelessly transmits a pulse signal to the SAW-based micro sensor 10 to measure variances in environmental elements. Whenever an interval between the plurality of pulse signals received by reflecting the transmitted pulse signal by the SAW micro sensor 10 is corresponding to a determined interval between pulse signals of an environmental element, the reader 20 generates and wirelessly transmits a pulse signal to the SAW-based micro sensor 10 and measures a variance in the environmental element by counting times of pulse signals generated for a certain amount of time.

The reader 20 includes a radio frequency (RF) part 21 and an environmental element variance measurement part 24.

The environmental element variance measurement part 24 generates and transmits a pulse signal for measuring a variance of an environmental element to the SAW-based micro sensor 10 via the RF part 21. Whenever an interval between the plurality of pulse signals received by reflecting the transmitted pulse signal by the SAW micro sensor 10 is corresponding to a determined interval between pulse signals of an environmental element, the environmental element variance measurement part 24 generates and wirelessly transmits a pulse signal to the SAW-based micro sensor 10 via the RF part 21 and measures a variance in the environmental element by counting times of pulse signals generated for a certain amount of time.

The RF part 21 wirelessly transmits the pulse signal generated by the environmental element variance measurement part 24 to the SAW-based micro sensor 10, transmits the plurality of pulse signals wirelessly received from the SAW-based micro sensor 10 to the environmental element variance measurement part 24, and includes an antenna ANT, a transmitter 22, a receiver 23, a frequency synthesizer 25, a transmission/reception selecting switch (T/R SW) 26, and a duplexer 27. The antenna ANT wirelessly transmits and receives a pulse signal. The frequency synthesizer 25 outputs a signal having a frequency in a certain band. The transmitter 22 modulates the pulse signal generated by the environmental element variance measurement part 24 by using the signal outputted by the frequency synthesizer 25 and transmits the modulated signal to the SAW-based micro sensor 10 via the antenna ANT. The receiver 23 modulates the plurality of pulse signals reflected by the SAW-based micro sensor 10 and received via the antenna ANT by using the signal outputted by the frequency synthesizer 25 and transmits the modulated signals to the environmental element variance measurement part 24. The T/S selecting switch 26 connects the duplexer 27 and the receiver 24 to each other and transmits a plurality of pulse signals received via the antenna ANT to the receiver 23 by switching according to a certain reception-selecting signal or connects the duplexer 27 and the transmitter 22 to each other and transmits an signal outputted by the transmitter 22 to the antenna ANT by switching according to a certain transmission-selecting signal. In this case, the certain transmission-selecting signal may be generated the environmental element variance measurement part 24 when transmitting a pulse signal for measuring a variance of the environmental element, and the certain reception-selecting signal is for receiving a pulse signal reflected by the SAW-based micro sensor 10 to measure the variance of the environmental element and may be generated by the environmental element variance measurement part 24.

The duplexer 27 is connected to the antenna ANT and distinguishes signals transmitted and received by the RF part 21. That is, the duplexer 27 may include a band pass filter allowing only a frequency of a transmitted signal to pass and a band pass filter allowing only a frequency of a received signal to pass.

Figure 2:
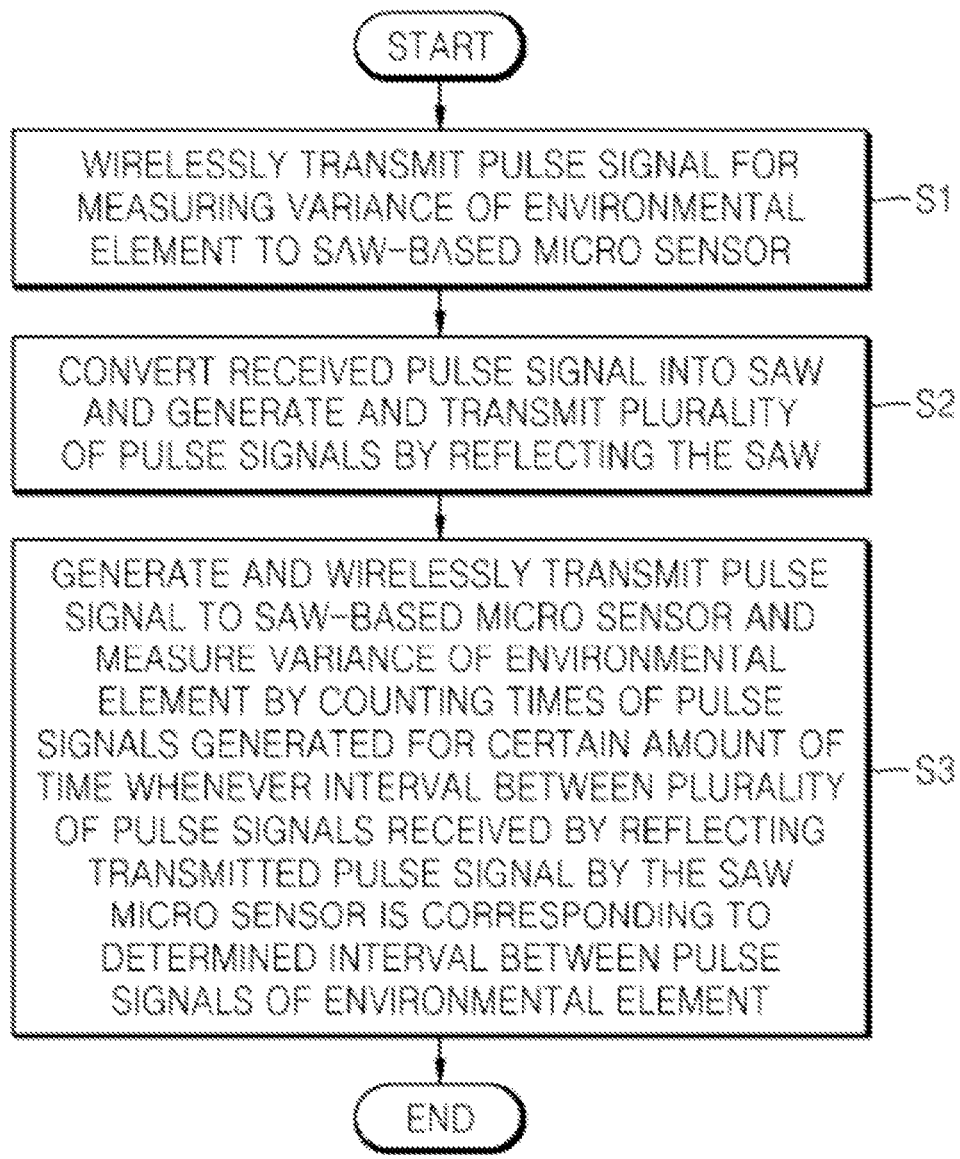
FIG. 2 is a flowchart illustrating a wireless measuring method using an SAW-based micro sensor according to an embodiment of the present invention.

FIG. 2 is a flowchart illustrating a method of wirelessly measuring by using the SAW-based micro sensor 10 according to an embodiment of the present invention.

The wirelessly measuring method shown in FIG. 2 may be performed by the wireless measurement device shown in FIG. 1. Accordingly, based on the configuration shown in FIG. 1, the method of wirelessly measuring by using the SAW-based micro sensor 10 will now be described.

The reader 20, to measure a variance of an environmental element, generates a pulse signal and wirelessly transmits the pulse signal to the SAW-based micro sensor 10 (S1).

The SAW-based micro sensor 10 converts the wirelessly received pulse signal into an SAW and to measure the variance of the environmental element, generates a plurality of pulse signals by reflecting the SAW, and wirelessly transmits the plurality of pulse signals (S2). In this case, the environmental element may be pressure, a temperature, humidity, etc.

The reader 20 generates and wirelessly transmits a pulse signal to the SAW-based micro sensor 10 and measures the variance of the environmental element by counting times of pulse signals generated for a certain amount of time whenever an interval between the plurality of pulse signals received by reflecting the transmitted pulse signal by the SAW micro sensor 10 is corresponding to a determined interval between pulse signals of the environmental element (S3).

While the present invention has been particularly shown and described with reference to exemplary embodiments thereof, it will be understood by those of ordinary skill in the art that various changes in form and details may be made therein without departing from the spirit and scope of the present invention as defined by the following claims.

INDUSTRIAL APPLICABILITY

The present invention may be applied to the field of wireless measurement devices using micro sensors.

What is claimed is:

1. A wireless measurement device comprising:
    a surface acoustic wave (SAW)-based micro sensor converting a wirelessly received pulse signal into an SAW and generating a plurality of pulse signals by reflecting the SAW, and wirelessly transmitting the plurality of pulse signals to measure a variance of an environmental element; and
    a reader generating and wirelessly transmitting a pulse signal to the SAW-based micro sensor to measure variances in environmental elements, whenever an interval between the plurality of pulse signals received by reflecting the transmitted pulse signal by the SAW-based micro sensor corresponds to a determined interval between pulse signals of an environmental element,
    wherein the reader measures a variance in the environmental element by counting times of pulse signals generated and wirelessly transmitted to the SAW-based micro sensor for a certain amount of time.

2. The wireless measurement device of claim 1, wherein the SAW-based micro sensor comprises:
    an antenna wirelessly transmitting and receiving a pulse signal;
    an inter-digital transducer (IDT) generating an SAW by applying the pulse signal received at the antenna to a plurality of metallic electrodes formed parallel to one another and converting a plurality of SAWs reflected by a reflector part into a plurality of pulse signals, and wirelessly outputting the plurality of pulse signals via the antenna; and
    the reflector part comprising a plurality of reflectors and reflecting the SAW generated by the IDT.

3. The wireless measurement device of claim 2, wherein the IDT has a single phase unidirectional transducer configuration.

4. The wireless measurement device of claim 1, wherein the reader comprises:
    an environmental element variance measurement part generating and transmitting a pulse signal for measuring a variance of an environmental element to the SAW-based micro sensor via an radio frequency (RF) part, whenever an interval between the plurality of pulse signals received by reflecting the transmitted pulse signal by the SAW-based micro sensor corresponds to a determined interval between pulse signals of an environmental element, wherein the environmental element variance measurement part measures a variance in the environmental element by counting times of pulse signals generated for a certain amount of time; and the RF part wirelessly transmitting the pulse signal generated by the environmental element variance measurement part to the SAW-based micro sensor and transmitting the plurality of pulse signals wirelessly received from the SAW-based micro sensor to the environmental element variance measurement part.

5. The wireless measurement device of claim 4, wherein the RF part comprises:

an antenna wirelessly transmitting and receiving a pulse signal;

a transmitter modulating the pulse signal generated by the environmental element variance measurement part and transmitting the modulated signal to the SAW-based micro sensor via the antenna; and a receiver modulating the plurality of pulse signals reflected by the SAW-based micro sensor and received via the antenna ANT and transmitting the modulated signals to the environmental element variance measurement part.

6. A method of wirelessly measuring by using an SAW-based micro sensor, the method comprising:

generating a pulse signal and wirelessly transmitting the pulse signal to the SAW-based micro sensor, performed by a reader, to measure a variance of an environmental element;

converting the wirelessly received pulse signal into an SAW, and to measure the variance of the environmental element, generating a plurality of pulse signals by reflecting the SAW, and wirelessly transmitting the plurality of pulse signals, performed by the SAW-based micro sensor; and generating and wirelessly transmitting a pulse signal to the SAW-based micro sensor and measuring the variance of the environmental element by counting times of pulse signals generated for a certain amount of time whenever an interval between the plurality of pulse signals received by reflecting the transmitted pulse signal by the SAW-based micro sensor corresponds to a determined interval between pulse signals of the environmental element, performed by the reader.

* * * * *